United States Patent [19]

Blaskie et al.

[11] 4,361,711
[45] Nov. 30, 1982

[54] ALCOHOLS FROM OLEFINS AND SYNTHESIS GAS

[75] Inventors: M. W. Blaskie, Shaker Heights; J. R. Fox, Solon; F. A. Pesa, Aurora, all of Ohio

[73] Assignee: The Standard Oil Company, Cleveland, Ohio

[21] Appl. No.: 332,036

[22] Filed: Dec. 18, 1981

[51] Int. Cl.³ .................... C07C 29/36; C07C 27/20
[52] U.S. Cl. ............................ 568/909; 252/470; 252/471; 252/472; 252/473
[58] Field of Search .......................... 568/909

[56] References Cited

U.S. PATENT DOCUMENTS

| | | | |
|---|---|---|---|
| 2,880,241 | 3/1959 | Hughes | 568/909 |
| 3,501,531 | 3/1970 | Wilkinson | 568/909 |
| 3,544,635 | 12/1970 | Kehoe et al. | 568/909 |
| 3,557,219 | 1/1971 | Kehoe et al. | 568/909 |
| 3,631,111 | 12/1971 | Tucci | 568/909 |
| 3,657,354 | 4/1972 | Asinger | 568/909 |
| 3,733,362 | 5/1973 | Biale | 568/909 |
| 3,937,742 | 2/1976 | Yoo | 568/909 |
| 3,980,583 | 9/1976 | Mitchell et al. | 568/909 |
| 4,018,834 | 4/1977 | Yoo | 252/459 |
| 4,045,492 | 8/1977 | Kniese et al. | 568/909 |
| 4,096,164 | 6/1978 | Ellgen et al. | 568/902 |
| 4,221,744 | 9/1980 | Unruh | 568/909 |
| 4,272,410 | 6/1981 | Huang | 252/465 |

*Primary Examiner*—Joseph E. Evans
*Attorney, Agent, or Firm*—John E. Miller, Jr.; Herbert D. Knudsen; Larry W. Evans

[57] ABSTRACT

Olefins, carbon monoxide and hydrogen are catalytically reacted with rhodium catalysts to produce alcohols in a single step reaction.

10 Claims, No Drawings

ALCOHOLS FROM OLEFINS AND SYNTHESIS GAS

BACKGROUND OF THE INVENTION

The present invention relates to a single-step, continuous, vapor phase process for producing alcohols by reacting olefins with carbon monoxide and hydrogen.

The catalytic hydroformylation of olefins to produce aldehydes and by-product alcohols is well known. See, for example, U.S. Pat. Nos. 2,880,241, 3,937,742, 4,018,834, 3,544,635 and 4,045,492.

Unfortunately, most processes produce a comparatively great amount of aldehydes and a correspondingly low amount of alcohols. In addition, most known processes produce a comparatively large amount of paraffins as by-products. Furthermore, most processes are conducted in the liquid phase in batch operation, which makes separation of the products from the reactants and catalysts difficult.

Accordingly, it is an object of the present invention to provide a new process for catalytically reacting olefins with carbon monoxide and hydrogen to produce alcohols which is capable of producing alcohols in large amounts with limited production of parafins and which can be carried out in the vapor phase on a continuous basis.

SUMMARY OF THE INVENTION

This and other objects are accomplished by the present invention which is based on the discovery that olefins can be catalytically reacted with carbon monoxide and hydrogen to produce alcohols in a single-step continuous, vapor phase procedure if the catalyst employed is a rhodium-containing oxide complex further containing an additional element selected from Fe, Zn, Ir, Ru, Nb, Cr, Mn and Pt.

Thus, the present invention provides a continuous process for directly converting a mono-olefin having no more than 16 carbons atoms to the corresponding alcohol comprising contacting the olefin together with carbon monoxide and hydrogen in the vapor phase at a temperature of at least 100° C. and a pressure of at least 150 psi with a solid oxide complex catalyst of the formula $$A_aRhO_x$$

wherein
A is Fe, Zn, Ir, Ru, Nb, Cr, Mn and/or Pt;
a is 0.001 to 10; and
x is greater than zero but less than a number sufficient to satisfy the valence requirements of the other elements present when in a fully oxidized state.

DETAILED DESCRIPTION

Reactants

In accordance with the present invention, any olefin having 18 or less carbon atoms can be reacted with carbon monoxide and hydrogen to produce the corresponding alcohol, i.e. an alcohol having one more carbon atom. Preferred mono-olefins are propylene and n-butylene.

Catalysts

The catalysts employed in the inventive process are oxide complexes of rhodium. They are solid materials, and for convenience can be defined by the following formula $$A_aRhO_x$$

wherein
A is Fe, Zn, Ir, Ru, Nb, Cr, Mn and/or Pt;
a is 0.001 to 10; and
x is greater than zero but less than a number sufficient to satisfy the valence requirements of the other elements present when in a fully oxidized state.
Preferably, A is Zn, Fe and/or Mn and a is 0.6 to 2.0.

The oxide complex catalysts of the invention can be used neat. However, it is preferred to support the oxide complexes on a conventional catalyst support. Materials such as silica, alumina, zirconia, kiesulgar, titania, molecular seives and the like can be employed, both in fixed-bed and fluid bed forms. Also the amount of oxide complex on the support is not critical, but is preferably such that the amount of rhodium on the support, measured as rhodium metal and based on total catalyst weight, is 0.1 to 40%, more preferably 2 to 8%, most preferably about 5%.

The catalysts of the invention can be prepared by any known catalyst preparation technique. Most conveniently they are prepared by impregnating the catalyst support with a liquid containing heat-decomposable salts of rhodium and the A element, drying and then calcining in air or other oxygen containing gas. Suitable heat-decomposable salts for supplying the rhodium are nitrates, oxides, hydroxides, halides, salts of organic acids such as acetates, formates and benzylates. Nitrates, oxalates and various organo metallic compounds can be employed for supplying the A element. The conditions for calcination are not critical so long as oxygen is present and the calcination conditions are severe enough to cause decomposition of the heat-decomposable salts and formation of an oxide complex from the rhodium and the A element. Typically, calcination can be carried out at 200° to 400° C. for ½ to 50 hours in air.

The oxide complexes when in use are in a reduced state. Thus they contain less oxygen than necessary to satisfy all of the valence requirements of the metals present if in a fully oxidized state, which is reflected in the definition of x in the formula. Reduction of the catalysts after calcination to an appropriate valence state will occur automatically by subjecting the fully oxidized oxide complexes to reaction conditions, the carbon monoxide and hydrogen in the reaction system causing the necessary reduction. Preferably, however, the fully oxidized oxide complex, prior to being subjected to reaction conditions, is subjected to a reducing regimen to accomplish catalyst reduction. Most conveniently, this is accomplished by contacting the catalyst with hydrogen either alone or together with an inert gas at an elevated temperature prior to charging the reactant mix into the system. For example, heating a fully oxidized catalyst at a temperature of 400° C. under an atmosphere of 100% $N_2$ for one hour followed by an atmosphere of 25% $H_2$/75% $N_2$ for an additional hour followed by an atmosphere of 100% $H_2$ for an additional hour has been found to be a very effective way to reduce the fully oxidized oxide complex. This technique is particularly advantageous because the reaction can be commenced simply by changing the temperature to the desired reaction temperature and then feeding the remaining reactants, the olefin and carbon monoxide, to the reaction system.

Process Conditions

The temperature of the reaction is not critical but should be above 50° C. Temperatures of 100° to 300° C. are preferred while temperatures of about 175° to 240° C. are even more preferred.

The ratio of reactants can vary widely. Usually, the $CO/H_2$ ratio will be between 10/1 and 1/10, preferably 4/1 to 1/4, more preferably 2/1 to 1/2. In addition, the ratio of olefin to synthesis gas ($CO+H_2$) can vary between 15/1 and 1/10, preferably 10/1 and 1/3, more preferably 3/1 and 1/1.5.

The pressure of the reaction can also vary widely, but should be at least about 100 psi. Pressures on the order of 150 to 2000 psig are preferred with pressures on the order of 800 to 1400 psig being even more preferred.

EXAMPLES

In order to more thoroughly illustrate the present invention, the following working examples are presented.

In each example, a 40 cc fixed-bed reactor was packed with 20 cc of catalyst and the remaining space was filled with 5 mm pyrex beads. Reduction of the catalyst was accomplished by first heating the reactor up to 400° C. while nitrogen gas was passed over the catalyst bed at 550 cc/min. After one hour hydrogen was added to the nitrogen stream at about 250 cc/min. This was continued for one-half hour at which time nitrogen flow was stopped and the hydrogen flow was increased by 50 cc/min. After heating at 400° C. for an additional hour, the reactor was cooled down to the desired reaction temperature. The system was pressurized to the run temperature with hydrogen and allowed to stabilize at the run temperature and pressure before the carbon monoxide was added. When this had occurred, carbon monoxide flow was initiated and then liquid propylene was pumped into the system on a continuous basis, the liquid propylene vaporizing as soon as it reached the reactor. Normally, a prerun of one hour duration was done to insure that the reaction had reached a steady state. The off gas from the reactor was passed through a condensor and into a cooled scrubber to collect any liquid products that might be present. After the prerun, the off gas from the condensor was switched to another scrubber to collect the liquid products from the run. At the end of the reaction, another gas sample was taken and the liquid products were collected, weighed and analyzed.

Each of the catalysts was prepared in the conventional manner as discussed above. For example, the catalyst of Example 12 was prepared as follows:

10 g of a silica gel pellet support was impregnated with 13 ml of an aqueous solution containing 1.82 g of $Rh(NO_3)_3.2\ H_2O$ and 1.02 g $Zn(NO_3)_2.6\ H_2O$. The loaded support was dried at 125° C. for approximately one hour and the dried pellets were calcined in air for three hours at 300° C. to give a catalyst of the composition $Zn_{0.6}RhO_x$ on a silica support. The catalyst was then loaded into the reactor and subjected to reduction as discussed above.

A number of catalysts in accordance with the present invention as well as catalysts containing only rhodium were tested. In all experiments the reaction pressure was 1100 psi and the feed rate was 3 CO/3 $H_2$/1 propylene and the total amount of rhodium present in the catalyst was 5.0 millimoles. The identity of the catalysts, the reaction temperature and pressure, the hydrogen flow rate, the contact time, the propylene conversion and the selectivity to different products are set forth in the following table:

TABLE I

| EX. NO. | CATALYST COMPOSITION | $R_x$ TEMP. °C. | $H_2$ FLOW RATE cc/min. | CONTACT TIME, sec | CONVERSION % | SELECTIVITY % | | | |
|---|---|---|---|---|---|---|---|---|---|
| | | | | | | isobutyr aldehyde | n-butyl aldehyde | isobutyl alcohol | n-butyl alcohol |
| A | Rh—Silica | 230 | 500 | 2.00 | 8.5 | 17.7 | 42.3 | — | 25.0 |
| B | Rh—Silica | 200 | 369 | 2.00 | 2.6 | 15.49 | 20.9 | 0.6 | 3.3 |
| C | Rh—Silica | 200 | 365 | 2.00 | 4.7 | 27.1 | 32.3 | 5.4 | 13.1 |
| D | Rh—Zirconia—Alumina | 150 | 450 | 2.00 | 2.7 | 30.2 | 53.9 | 0.7 | 2.3 |
| E | Rh—Silica | 200 | 364 | 2.00 | 1.1 | 17.7 | 21.7 | 6.08 | 8.2 |
| F | Rh—Silica | 230 | 364 | 1.80 | 4.4 | 16.3 | 24.2 | 9.5 | 16.6 |
| 1 | $RhZn_{1.5}$—Silica | 200 | 370 | 2.00 | — | — | — | 5.7 | 19.6 |
| 2 | $RhZn_{1.5}$—Silica | 230 | 374 | 2.00 | — | 7.1 | 1.1 | 17.5 | 64.2 |
| 3 | $RhZn_{1.5}$—Silica | 200 | 365 | 2.00 | 2.3 | 1.8 | 1.3 | 19.0 | 69.2 |
| 4 | $RhZn_{1.5}$—Silica | 200 | 370 | 2.00 | — | 1.6 | 1.2 | 20.0 | 70.1 |
| 5 | $RhZn_{1.5}$—Silica | 200 | 366 | 2.00 | 2.1 | 6.1 | 2.4 | 20.1 | 68.5 |
| 6 | RhRu—Silica | 200 | 363 | 2.00 | 4.3 | 17.7 | 26.8 | 8.6 | 19.2 |
| 7 | $RhMn_2$—Silica | 200 | 370 | 2.00 | 4.4 | 20.4 | 13.5 | 11.8 | 22.0 |
| 8 | $RhMn_2$—Silica | 190 | 405 | 2.00 | 3.5 | 17.4 | 27.1 | 7.6 | 20.4 |
| 9 | $RhFe_{1.8}$—Silica | 200 | 363 | 2.00 | 3.2 | 7.2 | 7.1 | 25.0 | 50.1 |
| 10 | $RhCr_2$—Silica | 200 | 373 | 2.00 | 3.7 | 16.0 | 26.2 | 10.6 | 27.0 |
| 11 | $RhPt_{0.5}$—Silica | 200 | 364 | 2.00 | 13.4 | 21.3 | 23.7 | 11.1 | 18.8 |
| 12 | $RhZn_{0.6}$—Silica | 200 | 365 | 2.00 | 2.6 | 6.9 | 2.7 | 18.2 | 61.5 |
| 13 | $RhZn_{0.6}$—Silica | 200 | 494 | 2.00 | 3.0 | 0.9 | 1.4 | 22.0 | 75.1 |
| 14 | $RhZn_{0.6}$—Silica | 220 | 382 | 2.00 | 4.5 | 1.0 | 1.6 | 21.3 | 75.0 |
| 15 | RhNb—Silica | 220 | 377 | 2.00 | 15.6 | 14.9 | 12.8 | 22.4 | 23.8 |
| 16 | RhIr—Silica | 200 | 369 | 2.00 | 6.9 | 9.1 | 3.0 | 17.5 | 31.4 |

From the above, it can be seen that propylene can be directly converted into the corresponding alcohol in a single-step continuous, vapor phase process, with the alcohols being produced in relatively high amounts compared to the aldehydes.

Although only a few embodiments of the invention are illustrated above, many modifications can be made without departing from the spirit and scope of the invention. All such modifications are intended to be within the scope of the present invention, which is to be limited only by the following claims:

We claim:

1. A continuous, vapor phase process for directly converting a mono-olefin having no more than 8 carbon atoms to an alcohol comprising contacting said olefin together with carbon monoxide and hydrogen in the vapor phase at a temperature of at least 100° C. and a pressure of at least 150 psig with a solid oxide complex of the formula $$A_a RhO_x$$

wherein

A is Fe, Zn, Ir, Ru, Nb, Cr, Mn and/or Pt;

a is 0.001 to 10; and x is greater than zero but less than a number sufficient to satisfy the valence requirements of the other elements present when in a fully oxidized state.

2. The process of claim 1 wherein A is Fe, Zn and/or Mn.

3. The process of claim 2 wherein A is Zn.

4. The process of claim 1 wherein said process is carried out at a temperature of 100° to 300° C. and a pressure of 150 to 2000 psig.

5. The process of claim 4 wherein said oxide complex is supported on a catalyst support.

6. The process of claim 5 wherein the amount of rhodium on said catalyst support is 0.1 to 40 wt %, measured as rhodium metal.

7. The process of claim 6 wherein the amount of rhodium on said support is 2 to 8 wt %, measured as rhodium metal.

8. The process of claim 6 wherein a is 0.6 to 2.0.

9. The process of claim 1 wherein the $CO/H_2$ ratio in the gas contacting said catalyst are 4/1 to 1/4 and the amount of $CO+H_2$ to olefins is 10/1 to 1/3.

10. The process of claim 1 wherein prior to contact with olefin said oxide complex catalyst is contacted with hydrogen to reduce the amount of oxygen therein.

* * * * *